United States Patent
Kataoka et al.

(10) Patent No.: US 8,895,076 B2
(45) Date of Patent: Nov. 25, 2014

(54) LIQUID COMPOSITION OF CISPLATIN COORDINATION COMPOUND

(75) Inventors: Kazunori Kataoka, Bunkyo-ku (JP);
Nobuhiro Nishiyama, Bunkyo-ku (JP);
Chieko Tsuchiya, Kashiwa (JP);
Tatsuyuki Hayashi, Kashiwa (JP)

(73) Assignees: Nanocarrier Co., Ltd., Kashiwa-shi (JP); The University of Tokyo, Tokyo (JP)

( * ) Notice: Subject to any disclaimer, the term of this patent is extended or adjusted under 35 U.S.C. 154(b) by 320 days.

(21) Appl. No.: 13/001,006

(22) PCT Filed: May 27, 2009

(86) PCT No.: PCT/JP2009/060102
§ 371 (c)(1),
(2), (4) Date: Jan. 25, 2011

(87) PCT Pub. No.: WO2009/157279
PCT Pub. Date: Dec. 30, 2009

(65) Prior Publication Data
US 2011/0110881 A1 May 12, 2011

(30) Foreign Application Priority Data
Jun. 24, 2008 (JP) ................................. 2008-164814

(51) Int. Cl.
| | | |
|---|---|---|
| *A61K 33/24* | (2006.01) | |
| *A61K 47/48* | (2006.01) | |
| *A61K 31/74* | (2006.01) | |
| *A61K 31/282* | (2006.01) | |
| *A61K 47/32* | (2006.01) | |
| *A61K 31/28* | (2006.01) | |
| *A01N 55/02* | (2006.01) | |
| *A61K 9/107* | (2006.01) | |
| *C08G 73/02* | (2006.01) | |
| *A61K 9/00* | (2006.01) | |
| *C08G 69/10* | (2006.01) | |
| *C08G 69/40* | (2006.01) | |
| *C08K 5/00* | (2006.01) | |

(52) U.S. Cl.
CPC ......... *A61K 47/488* (2013.01); *A61K 47/48215* (2013.01); *A61K 9/1075* (2013.01); *C08G 73/0233* (2013.01); *A61K 9/0019* (2013.01); *C08K 5/0091* (2013.01); *C08G 69/10* (2013.01); *C08G 69/40* (2013.01)

USPC ................ 424/649; 424/78.17; 424/78.08; 424/489; 514/492; 514/772.6

(58) Field of Classification Search
USPC ............ 424/649, 78.17, 78.08, 489; 514/492, 514/772.6
See application file for complete search history.

(56) References Cited

U.S. PATENT DOCUMENTS

| | | | |
|---|---|---|---|
| 5,925,720 A | 7/1999 | Kataoka et al. | |
| 5,929,177 A | 7/1999 | Kataoka et al. | |
| 5,973,069 A | 10/1999 | Kataoka et al. | |
| 7,125,546 B2 * | 10/2006 | Kataoka et al. ............ | 424/78.17 |
| 2003/0170201 A1 | 9/2003 | Kataoka et al. | |
| 2008/0166380 A1 | 7/2008 | Yamamoto et al. | |

FOREIGN PATENT DOCUMENTS

| | | |
|---|---|---|
| JP | 2003-12505 | 1/2003 |
| JP | 2003-12505 A * | 1/2003 |
| WO | WO 96/32434 | 10/1996 |
| WO | WO 96/33233 | 10/1996 |
| WO | WO 97/06202 | 2/1997 |
| WO | WO 02/26241 A1 | 4/2002 |
| WO | WO 2004/112757 A1 | 12/2004 |
| WO | WO 2006/057429 A1 | 6/2006 |
| WO | WO 2007/066781 A1 | 6/2007 |

OTHER PUBLICATIONS

Extended European Search Report dated Jun. 14, 2012 for corresponding European Patent Application No. 09769989.6, 6pp.
Yokoyama, Masayuki et al.; "Introduction of cisplatin into polymeric micelle"; Journal of Controlled Release; vol. 39; 1996; pp. 351-356.
Office action mailed on Sep. 24, 2013 in corresponding Japanese Patent Application No. 2010-517837, citing the listed references, 2pp.
Awazu, Shoji et al.; Saishin Yakuzaigaku; 7; 104-105; 1997; including partial machine translation; 3pp.
International Search Report, dated Aug. 25, 2009, corresponding to PCT/JP2009/060102, 3 pages.

* cited by examiner

*Primary Examiner* — John Pak
*Assistant Examiner* — Nathan W Schlientz
(74) *Attorney, Agent, or Firm* — Christie, Parker & Hale, LLP

(57) ABSTRACT

A liquid composition containing a polymer micelle and having a pH values of 3.0 to 7.0 is provided. The micelle is constituted of a coordination compound having a block copolymer of polyethylene glycol and polyglutamic acid and cisplatin that is coordinate-bonded to the block copolymer.

15 Claims, No Drawings

LIQUID COMPOSITION OF CISPLATIN COORDINATION COMPOUND

CROSS-REFERENCE TO RELATED APPLICATION

This application is a National Phase Patent Application and claims the priority of International Application Number PCT/JP2009/060102, filed on May 27, 2009, which claims priority of Japanese Patent Application Number 2008-164814, filed on Jun. 24, 2008.

TECHNICAL FIELD

The present invention relates to a stable liquid composition of a cisplatin coordination compound.

BACKGROUND ART

Although cisplatin (cis-diamine-dichloroplatinum (II)) is an extremely useful anticancer drug used in the clinical setting, it is known to have extremely potent adverse effects such as nephrotoxicity. Consequently, large-volume liquid infusion is required before, during and after administering cisplatin.

In order to resolve this problem, a coordination compound has been invented in which cisplatin is coordinate-bonded to a block copolymer consisting of polyethylene glycol and polyglutamic acid.

PRIOR ART DOCUMENTS

Patent Documents

Patent Document 1: WO 02/26241

SUMMARY OF THE INVENTION

Problems to be Solved by the Invention

The purpose of the present invention is to stabilize a liquid composition containing a coordination compound in which cisplatin is coordinate-bonded to a block copolymer consisting of polyethylene glycol and polyglutamic acid.

Means for Solving the Problems

As a result of employing extensive efforts to stabilize a complex in which cisplatin is coordinate-bonded to a block copolymer consisting of polyethylene glycol and polyglutamic acid, the inventors of the present invention found that the complex can be stabilized at a pH within a certain specific range, thereby leading to completion of the present invention.

Namely, the present invention includes the following aspects:

(1) a liquid composition, containing a coordination compound of a block copolymer represented by the following formula I or formula II:

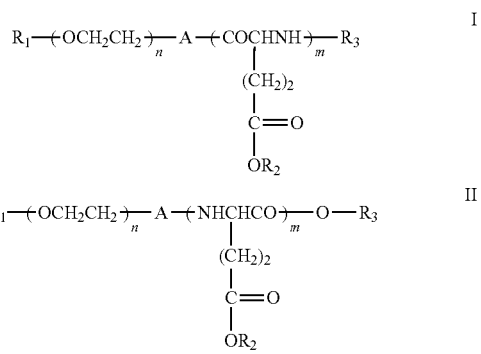

(wherein, $R_1$ independently represents a hydrogen atom or alkyl group optionally substituted by a functional group or substituent, A independently represents NH, CO, $R_5(CH_2)_pR_6$ or a direct bond, wherein $R_5$ represents O, OCO, OCONH, NHCO, NHCOO, NHCONH, CONH or COO, $R_6$ represents NH or CO, and p represents an integer of 1 to 6, $R_2$ independently represents a hydrogen atom, alkaline metal, alkyl group or aralkyl group, $R_3$ independently represents a hydrogen atom, hydroxyl group or hydrophobic residue, n represents an integer of 110 to 340, and m represents an integer of 20 to 80) and cisplatin, characterized in that the pH of the liquid composition is 3.0 to 7.0;
(2) the liquid composition described in (1), wherein the pH of the liquid composition is 4.0 to 6.0;
(3) the liquid composition described in (1) or (2), wherein the liquid composition further contains a sugar or sugar-alcohol;
(4) the liquid composition described in (3), wherein the sugar or sugar-alcohol is D-mannitol; and,
(5) the liquid composition described in (4), wherein the concentration of D-mannitol in the liquid composition is 5% (w/v).

EMBODIMENTS OF THE INVENTION

A coordination compound of a block copolymer and cisplatin as referred to in the present invention refers to a compound in which one or both of two chlorine ions in a molecule of cisplatin are replaced with a carboxyl anion of a block copolymer represented by formula I or formula II. A coordination compound in which the equivalence ratio of Pt of cisplatin to carboxyl anion of the copolymer (Pt/COO$^-$) is 0.3 or more is preferable for use as the coordination compound of the present invention.

In addition, the coordination compound of the present invention is able to form polymeric micelles in an aqueous medium.

In the block copolymer represented by formula I or formula II of the present invention, examples of the hydrophobic group referred to in $R_2$ include, but are not limited to, $C_8$-$C_{16}$ alkylcarbonyl, $C_8$-$C_{16}$ alkyl, phenylacetyl, benzyl, diphenylacetyl, benzhydryl, pyrenesulfonyl, pyrenyl, adamantyl and cholesteryl groups. These groups can be introduced by an acid chloride method or active ester method. Such hydrophobic groups may be useful in enhancing the self-association ability, namely the ability to form polymeric micelles, of a coordination compound in accordance with the present invention in an aqueous medium.

Examples of the optionally protected functional group referred to in $R_1$ include a hydroxyl group, acetal, ketal, aldehyde, sugar residue, maleimido group, carboxyl group, amino group, thiol group and active ester. A hydrophilic segment in the case $R_1$ represents a lower alkyl group substituted by an optionally protected functional group can be in accordance with that described in, for example, WO 96/33233, WO 96/32434 or WO 97/06202.

In addition, it goes without saying that n and m in the block copolymer represented by formula I or formula II of the present invention represent average values, and the following block copolymer is particularly preferable:

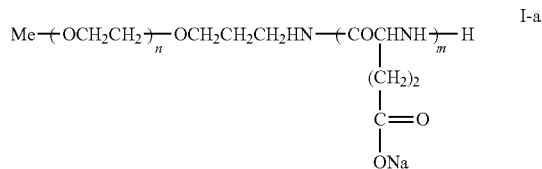

(wherein, although n represents an integer of 110 to 340, it particularly preferably represents an integer of 200 to 340, and although m represents an integer of 20 to 80, it particularly preferably represents an integer of 30 to 50).

The method of synthesizing the block copolymer represented by formula I, formula I-a or formula II is not limited as long as the desired block copolymer can be obtained. For example, the block copolymer represented by formula I-a can be synthesized through the following procedure. N-carboxy-γ-benzyl-L-glutamate is added and allowed to react in a dehydrated organic solvent so as to obtain the desired number of m units by using MeO—PEGOCH$_2$CH$_2$CH$_2$HN$_2$ as an initiator, and then a synthesized blockcopolymer is treated through an alkaline hydrolyzing of benzyl groups in the side chain of the polyglutamic acid that constitutes the synthesized blockcopolymer.

The liquid composition of the present invention refers to a liquid that contains said coordination compound, particularly polymeric micelles, and includes a preparation thereof, bulk liquid of such a preparation and such a liquid prior to carrying out freeze-drying.

An analogue of the present invention refers to a peak represented as a peak other than that of polymeric micelles when a coordination compound of a block polymer and cisplatin, which has formed polymeric micelles in an aqueous medium, has been measured by gel permeation chromatography (GPC), and has appeared as a decomposition product of the block copolymer and/or due to disintegration of the polymeric micelles, and the amount thereof can be represented as a percentage of the total area other than that attributable to the polymeric micelles in a GPC chart.

The pH of the liquid composition of the present invention is the pH at which the amount of analogue generated during storage of the polymeric micelles at 40° C. is 7% or less, preferably 5% or less and more preferably 3% or less, and that pH is preferably 3.0 to 7.0 and more preferably 4.0 to 6.0.

The liquid composition can be provided by using an additive that may be used to adjust the pH of an injection preparation as long as the pH of the composition is within the above ranges. For example, the pH may be adjusted by gradually adding the additive. Examples of the additive include hydrochloric acid, sodium hydroxide, citric acid, sodium citrate, acetic acid, tartaric acid, potassium hydroxide, sodium bicarbonate, sodium carbonate, lactic acid, triethanolamine, phosphoric acid, disodium hydrogen phosphate or sodium dihydrogen phosphate, to the liquid which contains a coordination compound, particularly polymeric micelles while stirring. Water is particularly preferable for the liquid containing polymeric micelles, but a dilute buffer solution may be used for the liquid as long as the coordinate bonds of the block copolymer and cisplatin is not disrupted.

EXAMPLES

The following provides a detailed explanation of the present invention through examples thereof. These examples are not intended to limit the scope of the present invention.

Example 1

Preparation of Polymeric Micelles

A solution in which 70 g of cisplatin were dissolved in water for injection, and a solution in which 105 g of a copolymer synthesized according to the method described in Patent Document 1 in the form of methoxypolyethylene glycol-polyglutamic acid copolymer, PEG-p(Glu) (average molecular weight of PEG was 12,000; average number of glutamic acid residues was 40; glutamic acid side chain was carboxylic acid) were dissolved in water for injection, were mixed followed by the addition of water for injection to bring to a volume of 50 L. This solution was allowed to react for 3 days at 37° C. The resulting solution was purified and concentrated by repeatedly subjecting to ultrafiltration (fraction molecular weight was 100,000) followed by the addition of D-mannitol and water for injection to obtain a polymeric micelle solution (equivalent to 2.5 mg/mL as cisplatin and containing 5% D-mannitol).

Example 2

Polymeric Micelle Stability Test 0.01 mol/L hydrochloric acid or 0.01 mol/L sodium hydroxide solution and water for injection were gradually added to 20 mL of the prepared polymeric micelle solution (equivalent to 2.5 mg/mL of cisplatin and containing 5% D-mannitol) to adjust the pH to 3.0, 4.0, 5.0, 6.0, 7.0 and 9.0 and bring to a total volume of 25 mL. Six mL of each pH solution were dispensed into brown vials, and then were sealed and stored at 5° C. Two days later, the amount of analogue was measured under the conditions indicated below, and the remaining solutions were transferred to a temperature of 40° C. and stored for an additional 20 days. After the storage, the amount of analogue was measured under the same conditions.

(Conditions)

Apparatus: Waters GPC System

Column: Waters Ultrahydrogel 500, 10 μm, 7.8φ×300 mm

Column temperature: Constant temperature of about 40° C.

Detector: UV detector (detection wavelength is 280 nm)

Mobile phase: 2.87 g of sodium dihydrogen phosphate (anhydrous), 0.24 g of disodium hydrogen phosphate dodecahydrate and 2.92 g of sodium chloride were dissolved in water and brought to a volume of 1 L Flow rate: Approx. 0.6 mL/min The results of measuring the amount of analogue after the storage of 2 days at 5° C. and of 20 days at 40° C. are shown in Tables 1 and 2, respectively.

TABLE 1

| | Initially adjusted pH | | | | | |
|---|---|---|---|---|---|---|
| | 3.0 | 4.0 | 5.0 | 6.0 | 7.0 | 9.0 |
| Total amount of analogue (%) | 1.6 | 1.1 | 0.6 | 0.46 | 0.46 | 1.16 |

TABLE 2

| | Initially adjusted pH | | | | | |
|---|---|---|---|---|---|---|
| | 3.0 | 4.0 | 5.0 | 6.0 | 7.0 | 9.0 |
| Total amount of analogue (%) | 6.8 | 2.7 | 1.9 | 2 | 5.75 | 75.63 |

As illustrated in the above results, liquid compositions containing a polymer micelle, which is formed from a coordination compound of a block copolymer and cisplatin at a pH in a range of 3.0 to 7.0, particularly the range of 4.0 to 6.0, were extremely stable even if stored under harsh storage conditions such as 20 days at 40° C.

The invention claimed is:

1. A liquid composition, comprising a coordination compound of a block copolymer represented by the following formula I or formula II:

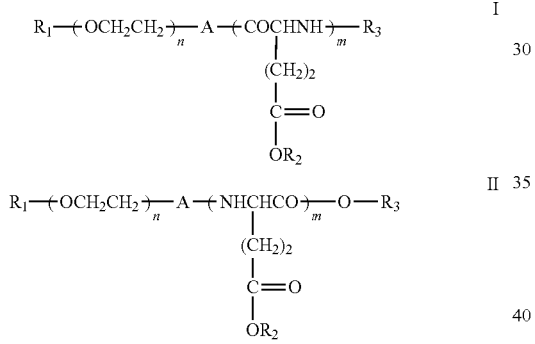

wherein, $R_1$ independently represents a hydrogen atom or alkyl group optionally substituted by a functional group or substituent, A independently represents NH, CO, $R_5(CH_2)_pR_6$ or a direct bond, wherein $R_5$ represents O, OCO, OCONH, NHCO, NHCOO, NHCONH, CONH or COO, $R_6$ represents NH or CO, and p represents an integer of 1 to 6, $R_2$ independently represents a hydrogen atom or an alkali metal, $R_3$ independently represents a hydrogen atom, hydroxyl group or hydrophobic residue, n represents an integer of 110 to 340, and m represents an integer of 20 to 80; and cisplatin, wherein the pH of the liquid composition is 4.0 to 6.0.

2. The liquid composition according to claim 1, wherein the liquid composition further comprises a sugar or sugar-alcohol.

3. The liquid composition according to claim 2, wherein the sugar or sugar-alcohol is D-mannitol.

4. The liquid composition according to claim 3, wherein the concentration of D-mannitol in the liquid composition is 5% (w/v).

5. The liquid composition according to claim 1, further comprising water.

6. The liquid composition according to claim 1, wherein the coordination compound is in an aqueous medium.

7. The liquid composition according to claim 1, wherein an amount of analogues of the coordination compound in the liquid composition is 3% or less, after storage of the liquid composition for twenty days at 40° C.

8. The liquid composition according to claim 1, wherein an amount of analogues of the coordination compound in the liquid composition is 2.7% or less, after storage of the liquid composition for twenty days at 40° C.

9. The liquid composition according to claim 1, wherein $R_1$ represents a hydrophilic alkyl group and $R_3$ represents a hydrogen atom or hydroxyl group.

10. An injection preparation comprising the liquid composition according to claim 1, wherein the coordination compound is in an aqueous medium.

11. A liquid composition, comprising a coordination compound of a block copolymer represented by the following formula I or formula II:

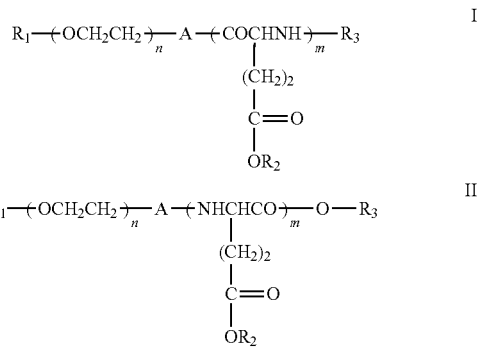

wherein, $R_1$ represents a hydrophilic segment, A represents $R_5(CH_2)_pR_6$, wherein $R_5$ represents O, $R_6$ represents NH, and p represents an integer of 1 to 6, $R_2$ represents a hydrogen atom or an alkali metal, $R_3$ represents a hydrogen atom, n represents an integer of 200 to 340, and m represents an integer of 30 to 50; and cisplatin, wherein the pH of the liquid composition is 4.0 to 6.0.

12. The liquid composition according to claim 11, wherein one or both chlorine atoms of the cisplatin are replaced with carboxyl anions of the block copolymer represented formula I.

13. The liquid composition according to claim 11, wherein the coordination compound is in an aqueous medium.

14. A liquid composition, comprising a coordination compound formed from cisplatin and a methoxypolyethylene glycol-polyglutamic acid copolymer, wherein:
   the methoxypolyethylene glycol-polyglutamic acid copolymer has an average number of glutamic acid residues of 40,
   the glutamic acid residues have carboxylic acid side chains,
   one or both chlorine atoms of the cisplatin are replaced with carboxyl anions of the methoxypolyethylene glycol-polyglutamic acid copolymer
   and the pH of the liquid composition is 4.0 to 6.0.

15. The liquid composition according to claim 14, wherein the coordination compound is in an aqueous medium.

* * * * *